US008476196B2

(12) United States Patent
Paul, III et al.

(10) Patent No.: US 8,476,196 B2
(45) Date of Patent: Jul. 2, 2013

(54) CONTROL OF HARMFUL ALGAL BLOOMS BY INDUCTION OF PROGRAMMED CELL DEATH

(75) Inventors: John H. Paul, III, St. Petersburg, FL (US); David John, Clearwater, FL (US)

(73) Assignee: University of South Florida, Tampa, FL (US)

( * ) Notice: Subject to any disclaimer, the term of this patent is extended or adjusted under 35 U.S.C. 154(b) by 253 days.

(21) Appl. No.: 12/831,065

(22) Filed: Jul. 6, 2010

(65) Prior Publication Data

US 2011/0021357 A1 Jan. 27, 2011

Related U.S. Application Data

(60) Provisional application No. 61/223,288, filed on Jul. 6, 2009.

(51) Int. Cl.
A01N 59/00 (2006.01)
(52) U.S. Cl.
USPC .......................................................... 504/151
(58) Field of Classification Search
None
See application file for complete search history.

(56) References Cited

U.S. PATENT DOCUMENTS

| 6,918,354 | B2 | 7/2005 | Perriello |
| 6,921,488 | B1 | 7/2005 | Jelmert |
| 7,422,857 | B2 | 9/2008 | Paul, III |
| 2006/0289364 | A1* | 12/2006 | Wakao et al. ........... 210/753 |
| 2007/0111243 | A1* | 5/2007 | Paul, III ................. 435/6 |
| 2009/0075286 | A1 | 3/2009 | Paul, III |

FOREIGN PATENT DOCUMENTS

WO    WO 2008041470 A1 *  4/2008

OTHER PUBLICATIONS

Zhang et al., "Study on patterns and chemical features of NO effect on marine phytoplankton growth," Science in China Ser. B Chemistry 48:376 (2005).*
Bouchard, J.N. et al. "Implication of nitric oxide in the heat-stress-induced cell death of the symbiotic alga *Symbiodinium microadriatcum*" Mar Biol, Jul. 2009, 156:2209-2220.
"Nitric Oxide Donors and Scavengers", Calbiochem Technical Bulletin CB0562-0601, pp. 1-4, 2001.
Chung, C.C. et al. "Nitric Oxide as a Signaling Factor to Upregulate the Death-Specific Protein in a Marine Diatom, *Skeletonema costatum*, during Blockage of Electron Flow in Photosynthesis" *Applied and Environmental Microbiology*, Nov. 2008, 74(21):6521-6527.
Jiménez, C. et al. "Different ways to die: cell death modes of the unicellular chlorophyte *Dunaliella viridis* exposed to various environmental stresses are mediated by the caspase-like activity DEVDase" *Journal of Experimental Botany*, 2009, 60(3):815-828.
John, D. et al. "Biological Control of Harmful Algal Blooms" presented at Florida HAB Control and Mitigation Workshop, held Feb. 9-11, 2010, at the Mote Marine Laboratory, Sarasota, Florida, 27 pages.

(Continued)

*Primary Examiner* — James H Alstrum Acevedo
*Assistant Examiner* — Thor Nielsen
(74) *Attorney, Agent, or Firm* — Saliwanchik, Lloyd & Eisenschenk

(57) ABSTRACT

The subject invention pertains to compositions, apparatus, and methods for controlling harmful algae and harmful algal bloom (HAB) based on the induction of the programmed cell death (PCD; apoptosis) pathway in the harmful algae, and to kits for determining algal susceptibility to PCD induction.

16 Claims, 4 Drawing Sheets

OTHER PUBLICATIONS

Segovia, M. et al. "Inhibition of Caspase-Like Activities Prevents the Appearance of Reactive Oxygen Species and Dark-Induced Apoptosis in the Unicellular Chlorophyte *Dunaliella tertiolecta*" *J. Phycol.*, 2009, 45:1116-1126.

Wang, P.G. et al. "Nitric Oxide Donors: Chemical Activities and Biological Applications" *Chem. Rev.* 2002, 102(4):1091-1134.

Zhang, Z.B. et al. "The Effect of Nitric Oxide on the Growth of Marine Phytoplankton" *Journal of Ocean University of Qingdao*, Oct. 2003 2(2):185-188.

Casper, E.T. et al. "Detection and Quantification of the Red Tide Dinoflagellate *Karenia brevis* by Real-Time Nucleic Acid Sequence-Based Amplification" *Applied and Environmental Microbiology*, Aug. 2004, 70(8):4727-4732.

Casper, E.T. et al. "A handheld NASBA analyzer for the field detection and quantification of *Karenia brevis*" *Harmful Algae*, 2007, 6(1):112-118.

* cited by examiner

CONTROL OF HARMFUL ALGAL BLOOMS BY INDUCTION OF PROGRAMMED CELL DEATH

CROSS-REFERENCE TO RELATED APPLICATION

The present application claims the benefit of U.S. Application Ser. No. 61/223,288, filed Jul. 6, 2009, which is hereby incorporated by reference herein in its entirety, including any figures, tables, nucleic acid sequences, amino acid sequences, and drawings.

GOVERNMENT SUPPORT

This invention was made with government support under National Oceanic & Atmospheric Administration grant number NA06NOS4780230. The government has certain rights in the invention.

BACKGROUND OF THE INVENTION

By conservative estimates, harmful algal blooms (HABs) cost the United States $50 million per year (Hoagland, P. et al. *Estuaries*, 2002, 25:819-837). Such estimates are based upon direct economic impacts on tourism, fisheries, etc., and do not account for irremediable costs such as those caused by mass marine mammal mortalities (Landsberg, J. H. *Rev. Fish. Sci.*, 2002, 10:113-390; Landsberg, J. H. and Steidinger, K. A. "A historical review of *Gymnodinium breve* red tides implicated in mass mortalities of the manatee (*Trichechus mantus latirostris*) in Florida, USA", 1998, pp. 97-100, in B. Reguera et al. Eds, Proceedings of the 8$^{th}$ International Conference on Harmful Algae, Xunta de Galicia and Intergovernmental Oceanographic Commission of UNESCO, Vigo, Spain). Worldwide, algal toxins of all types may be responsible for as many as 60,000 human intoxication events per year (Van Dolah, F. M. et al. *Hum. Ecol. Risk Assess.*, 2001, 7:1329-1345).

Nearly all coastal regions of the United States are impacted by HABs for various intervals in time and intensity. Perhaps no coastal environment has a frequency of HABs equal to that of the Florida Gulf Coast, caused by the non-peridinin dinoflagellate *Karenia brevis* (Davis) cf. Hansen and Moestrup (*Gymnodinium breve*). Although red tides have been observed in the Gulf of Mexico since the Spanish Conquests and reports of catastrophic fish mortalities go back to 1844, the identity of *K. brevis*, initially named *G. breve*, as the causative agent was not determined until the bloom of 1946 to 1947 (Gunther, G. et al. *Ecol. Monogr*, 1948, 18:311-324). In certain years, red tides have occurred during 12 months of the year, although they are most often encountered in the late summer and early fall, correlating with heavy rainfall (Landsberg, J. H. *Rev. Fish. Sci.*, 2002, 10:113-390).

Efforts to control HABs have been hampered by limited research on the subject, particularly with respect to the monitoring and prediction of HABs. Historically, blooms have occurred primarily during the fall and winter months. Over recent years, however, the Florida red tide specifically, and HABs in general, appear to be more prevalent and widespread (Chretiennot-Dinet, M., *Oceanis*, 2001, 24:223-238; Hallegraeff, G. M., *Phycologia*, 1991, 32:79-99). Massive fish kills, marine mammal mortalities, human poisonings due to the consumption of tainted shellfish and complaints of respiratory irritations among beach-goers are associated with these blooms (Kirkpatrick et al., *Harmful Algae*, 2004, 3:99-115; Van Dolah et al., in Toxicology of Marine Mammals, Taylor & Francis, Inc., 2002, Vos et al. (Eds.), p. 247-269). These harmful effects are attributed to a suite of polyketide secondary metabolites known as brevetoxins, which are part of a larger family of dinoflagellate-derived polyketide toxins that pose a threat to human health. Brevetoxins are polyether ladder type compounds having two parent backbone structures, brevetoxin A and brevetoxin B, each with several side-chain variants. Examples of other harmful polyketide toxins include ciguatoxin, okadaic acid, and the related kinophysis-toxins, pectenotoxins, yessotoxin, and the azaspiracids. The mechanism of synthesis of brevetoxins is unknown but is hypothesized to be the result of enzymes similar to polyketide synthetases. Recently, two polyketide synthetase genes were described from *K. brevis* (Snyder et al. *Mar. Biotechnol.*, 2003, 5:1-12; Snyder et al. *Phytochemistry*, 2005, 66(15): 1767-80).

A myriad of approaches have been taken to address the problem of HAB monitoring and prediction, including satellite ocean color sensing (Stumpf, R. P. *Hum. Ecol. Risk Assess.*, 2001, 7:1363-1368), photopigment analysis (Millie, D. F. et al. *Limnol. Oceanogr.*, 1997, 42:1240-1251; Millie, D. F. et al. *J. Phycol.*, 2001, 37:35; Oernolfsdottir, E. B. et al. *J. Phycol.*, 2003, 39:449-457), and toxin analysis (Pierce, R. H. and Kirkpatrick, G. J. *Environ. Toxicol. Chem.*, 2001, 20:107-114). Additionally, molecular methods are being developed to detect a variety of HAB species, including *Alexandrium* sp. (Adachi, M. et al. *J. Phycol.*, 1996, 32:1049-1052; Godhe, A. et al. *Mar. Biotechnol.*, 2001, 3:152-162), *Gymnodinium* sp. (Godhe, A. et al. *Mar. Biotechnol.*, 2001, 3:152-162; Peperzak, L. et al. "Application and flow cytometric detection of antibody and rRNA probes to *Gymnodinium mikimotoi* (Dinophyceae) and *Pseudo-nitzschia multiseries* (Bacillariophyceae), 2000, pp. 206-209, in G. M. Hallegraff et al. Eds., Harmful algal blooms, IOC-UNESCO, Paris, France), *Pseudonitzschia* sp. (Peperzak, L. et al. "Application and flow cytometric detection of antibody and rRNA probes to *Gymnodinium mikimotoi* (Dinophyceae) and *Pseudo-nitzschia multiseries* (Bacillariophyceae), 2000, pp. 206-209, in G. M. Hallegraff et al. Eds., Harmful algal blooms, IOC-UNESCO, Paris, France), *Pfiesteria* sp., and *Pfiesteria*-like organisms (Litaker, R. W. et al. *J. Phycol.*, 2003, 39:754-761) as well as *K. brevis* (Gray, M. et al. *Appl. Environ. Microbiol.*, 2003, 69:5726-5730; Loret, P. et al. *J. Plankton Res.*, 2002, 24:735-739).

Nucleic acid sequence-based amplification (NASBA) is an isothermal method of RNA amplification that has been previously used in clinical diagnostic testing. Recently, a real-time NASBA assay was developed for the detection of ribulose-1,5-bisphosphate carboxylase-oxygenase (RuBisCO) large-subunit (rbcL) mRNA from *K. brevis* (Casper et al., *Applied and Environmental Microbiology*, 2004, August, 70(8):4727-4732; Casper et al., *Harmful Algae*, 2006, 6(1): 112-118). The rbcL mRNA was selected as the target because cellular levels of mRNA are typically high and RNA degrades quickly in the environment, resulting in detection of viable *K. brevis* populations only. NASBA RNA amplification occurs at 41° C. (European Patent No. EP 0329822, Davey et al.). RNA is amplified by use of an enzyme cocktail including T7 RNA polymerase, avian myeloblastosis virus reverse transcriptase, RNaseH, and two target-specific oligonucleotide primers. A NASBA-based assay for *K. brevis* polyketide synthesis mRNA has been used to successfully detect and quantify *K. brevis* in cultures and field samples collected from the coastal waters of southwest Florida (U.S. Pat. No. 7,422,857, Paul, J., issued to the University of South Florida).

Approaches to direct HAB intervention can be grouped into three categories: mechanical, physical/chemical, and biological control. Mechanical control involves the use of filters, pumps, and barriers (such as curtains and floating booms) to remove or filter HAB cells, dead fish, or other bloom-associated materials from impacted waters. Physical/ chemical control involves the use of chemical or mineral compounds to kill, inhibit, or remove HAB cells. Biological control involves the use of organisms or pathogens (such as viruses, bacteria, parasites, zooplankton, or shellfish) that can kill, lyse, or remove HAB cells.

There exists a continuing need for a mitigation system that is effective in controlling and managing an HAB and harmful algae. An important criterion for any effective HAB control system is that the benefits of using the intervention outweigh collateral damage such as threats to public health and environmental impacts.

BRIEF SUMMARY OF THE INVENTION

The present inventors have determined that nitric oxide (nitrogen monoxide; NO) may be used to induce programmed cell death (PCD; apoptosis) in harmful algae, such as *Karenia brevis*. The present invention provides compositions and methods for controlling harmful algae such as *Karenia brevis*, and harmful algal bloom (HAB), based on the induction of the PCD pathway in the harmful algae. In some embodiments, the method of the invention comprises inducing the PCD pathway in the harmful algae such that the algae or HAB is controlled (e.g., mitigated, terminated, or otherwise inhibited). PCD induction can be achieved by application of any chemical or physical agent or treatment that induces the PCD pathway in the harmful algae.

In some embodiments, the method of the invention comprises applying an effective amount of a PCD inducer to the harmful algae, the aquatic medium or other situs that the algae inhabit or potentially inhabit, or both. Any method for bringing the PCD inducer and the algae (and/or situs) into contact may be utilized. The PCD inducer can be any agent or treatment that induces PCD in the harmful algae. For example, the PCD inducer may be one or more oxidizing agents and/or nitric oxide delivery agents. The PCD inducer may be applied to the algae and/or situs before an HAB has formed (e.g., as a preventative) or after HAB formation.

In some embodiments, the method of the invention comprises contacting the harmful algae, the aquatic medium or other situs that the algae inhabit or potentially inhabit, or both, with an algaecidally effective amount of nitric oxide. For example, nitric oxide can be bubbled into the aquatic medium or other situs that the algae inhabit or potentially inhabit.

The aquatic medium can be marine, fresh, or brackish (e.g., estuarine) water. The aquatic medium or other situs to which the PCD inducer is applied can be natural or in the environment, such as an area of ocean or bay, or artificial, such as an aquaculture system, aquarium, field sample, filter media, pool, ballast water, etc.

Another aspect of the invention concerns compositions for controlling harmful algae and HAB. The compositions of the invention comprise one or more PCD inducers, such as an oxidizing agent and/or a nitric oxide delivery agent, and another component selected from among: (a) another algaecidal agent, or (b) an activator of the PCD inducer (if an activation is desired or necessary), or (c) a dispersant, or a combination of two or more of the foregoing.

Another aspect of the invention concerns kits for determining algal susceptibility to PCD induction, comprising one or more PCD inducers and one or more reagents useful for determining the presence of one or more harmful algae. In some embodiments, the kits comprise reagents for determining the presence of a plurality of HAB species.

Another aspect of the invention includes an apparatus for control of harmful algae and HAB, comprising an injector for release of an inducer of programmed cell death (PCD inducer) and a source of a PCD inducer, such as an NO source, wherein the injector is in flow communication with said. PCD inducer source. Preferably, the injector is adapted to occupy the situs or potential situs of the harmful algae. The injector may be stationary, or part of a mobile device that moves through the situs (e.g., up and down a water column). In some embodiments, the apparatus further comprises a sensor for detecting the presence of harmful algae within the situs. Optionally, the sensor is in operable communication with the injector such that a PCD inducer is released from the injector into the situs upon detection of harmful algae by the sensor.

BRIEF DESCRIPTION OF THE DRAWINGS

FIG. 2A shows images of intact *K. brevis* cells from un-treated control flask collected at day 2 post-treatment. These photographs capture a range of angles and focal planes for intact cells. FIG. 2B shows images of disrupted *K. brevis* cells from a treated flask (100 µM DEA NONO final concentration). All cells imaged from treated flasks resembled these disrupted cells.

DETAILED DISCLOSURE OF THE INVENTION

Figure 1:
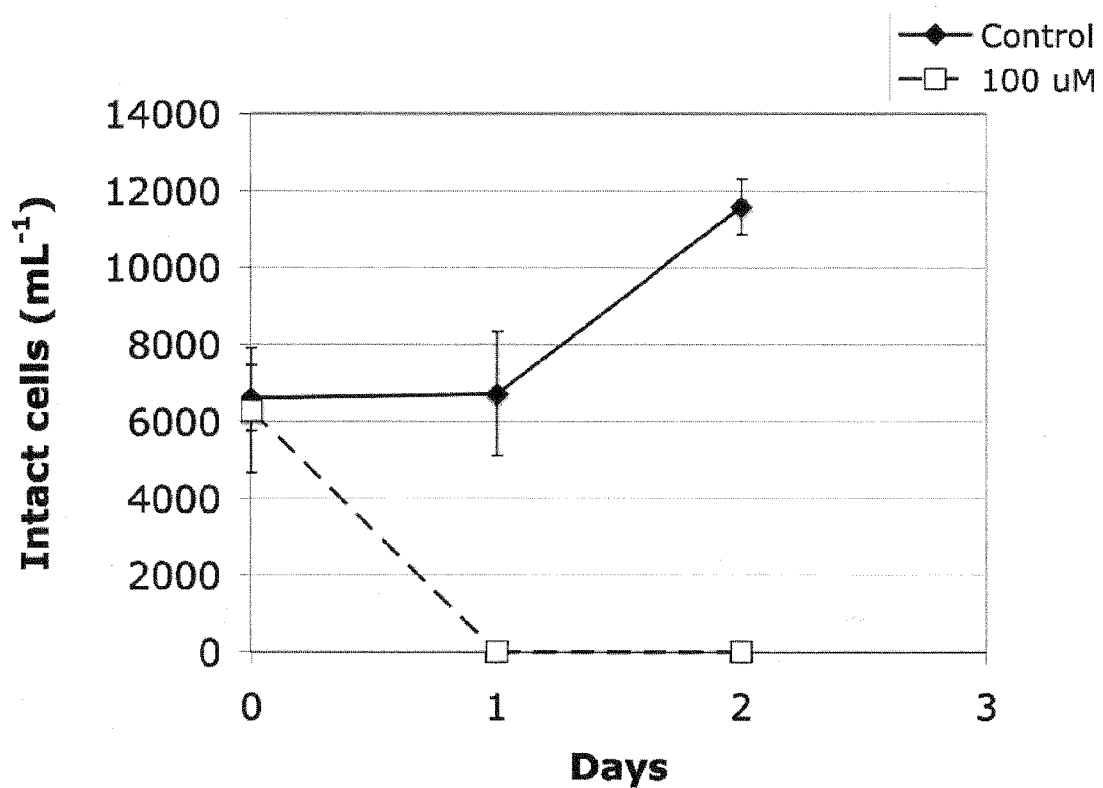
FIG. 1 shows results of *K. brevis* culture with 100 µM nitric oxide (NO). At 100 µM NO there was complete cell death at 24 hours. Three replicate flasks are averaged for each concentration. Error bars are 1 standard deviation about the average. In the treated flasks (100 µM NO), no intact cells were present after 1 day, nor at 2 days post-treatment.

The present invention provides compositions and methods for controlling harmful algae and harmful algal bloom (HAB) based on exploitation of the PCD pathway. One aspect of the invention is a method for controlling harmful algae and HAB inducing the PCD pathway in the harmful algae such that the algae or HAB is controlled (e.g., mitigated, terminated, or otherwise inhibited). PCD induction can be achieved by application of any chemical or physical agent or treatment that induces the PCD pathway in the harmful algae.

In some embodiments, the method for controlling harmful algae and HAB comprises applying an algaecidally effective amount of a PCD inducer to the algae, the aquatic medium or other situs that the algae inhabit or potentially inhabit, or both. Any method for bringing the PCD inducer and the algae (and/or situs) into contact may be utilized. The PCD inducer can be any agent or treatment that induces PCD in the harmful algae. For example, the PCD inducer may be one or more oxidizing agents and/or nitric oxide delivery agents. The PCD inducer may be applied to the algae and/or situs before an HAB has formed (e.g., as a preventative) or after HAB formation.

In some embodiments, the PCD inducer comprises NO. Thus, in some embodiments, the method for controlling harmful algae and HAB comprises contacting the harmful algae, the aquatic medium or other situs that the algae inhabit or potentially inhabit, or both, with an algaecidally effective amount of nitric oxide. For example, nitric oxide can be bubbled into the aquatic medium or other situs that the algae inhabit or potentially inhabit, to mitigate the algae infestation and potential HAB.

In addition to *K. brevis*, other examples of harmful algae and HAB species to which the methods, compositions, and kits can be applied include *Alexandrium* species, *Gymnodinium* species, *Karenia mikimotoi*, *Pseudo-nitzschia* species, *Karenia seleniformes*, *Karenia bidigigata*, *Pyrodininum* species, *Gonyaulax* species, *Ceratium* species, *Lingulodinium*, *Chattonella* species, *Akashiwo* species, *Gyrodinium* species, *Pfisteria* species, *Prorocentrum* species, *Dinophysis*, *Heterocapsa*, *Scripssiella*, and *Protoperidinium* species.

In some embodiments, the harmful algae is not one or more algae selected from the group consisting of *Skletonema costatum*, *Dicrateria zhanjiangensis nov.* sp., *Platymonas subcordiformis*, and *Emiliania huxleyi*.

The aquatic medium can be marine, fresh, or brackish (e.g., estruarine) water. The aquatic medium or other situs to which the PCD inducer is applied can be natural or artificial. The situs can be a closed water system or open water. Thus, application of a PCD inducer to a situs can involve broad deployment (e.g., several square miles across and throughout the water column) local deployment (e.g., a shellfish bed such as an oyster bed). For example, the situs can be a culture or field sample, an area of an ocean, bay, estuary, pond, lagoon, lake, river, stream, canal, aquarium, aquaculture system, waste water, cooling tower, water holding or conveying system (e.g., reservoir or ballast water), pool, spa, fountain, etc. In some embodiments, the situs is an area of water having a shellfish bed (e.g., an oyster bed), and the PCD inducer is applied to the situs, as a treatment, in which harmful algae is already present (a contaminated zone), and/or as a preventative, to protect the situs from harmful algae that are not yet present.

Optionally, the methods of the invention include a step of determining whether one or more harmful algae (such as *K. brevis*) or HAB are present at, or in the vicinity of, a situs in question before, during, and/or after application of the PCD inducer. These methods can employ, for example, satellite ocean color sensing (Stumpf, R. P. *Hum. Ecol. Risk Assess.*, 2001, 7:1363-1368), photopigment analysis (Millie, D. F. et al. *Limnol. Oceanogr.*, 1997, 42:1240-1251; Millie, D. F. et al. *J. Phycol.*, 2001, 37:35; Oernolfsdottir, E. B. et al. *J. Phycol.*, 2003, 39:449-457), and toxin analysis (Pierce, R. H. and Kirkpatrick, G. J. *Environ. Toxicol. Chem.*, 2001, 20:107-114). Additionally, molecular methods may be used to detect a variety of HAB species, including *Alexandrium* sp. (Adachi, M. et al. *J. Phycol.*, 1996, 32:1049-1052; Godhe, A. et al. *Mar. Biotechnol.*, 2001, 3:152-162), *Gymnodinium* sp. (Godhe, A. et al. *Mar. Biotechnol.*, 2001, 3:152-162; Peperzak, L. et al. "Application and flow cytometric detection of antibody and rRNA probes to *Gymnodinium mikimotoi* (Dinophyceae) and *Pseudo-nitzschia* multiseries (Bacillariophyceae), 2000, pp. 206-209, in G. M. Hallegraff et al. Eds., Harmful algal blooms, IOC-UNESCO, Paris, France), *Pseudonitzschia* sp. (Peperzak, L. et al. "Application and flow cytometric detection of antibody and rRNA probes to *Gymnodinium mikimotoi* (Dinophyceae) and *Pseudo-nitzschia* multiseries (Bacillariophyceae), 2000, pp. 206-209, in G. M. Hallegraff et al. Eds., Harmful algal blooms, IOC-UNESCO, Paris, France), *Pfiesteria* sp., and *Pfiesteria*-like organisms (Litaker, R. W. et al. *J. Phytol*, 2003, 39:754-761) as well as *K. brevis* (Gray, M. et al. *Appl. Environ. Microbiol.*, 2003, 69:5726-5730; Loret, P. et al. *J. Plankton Res.*, 2002, 24:735-739).

A real-time NASBA assay has been developed for the detection of ribulose-1,5-bisphosphate carboxylase-oxygenase (RuBisCO) large-subunit (rbcL) mRNA from *K. brevis* (Casper et al., *Applied and Environmental Microbiology*, 2004, August, 70(8):4727-4732; Casper et al., *Harmful Algae*, 2006, 6(1):112-118). Methods for detection of *K. brevis* are described, for example, in U.S. Pat. No. 7,422,857 (Paul J. H. III, issued to University of South Florida) and U.S. Patent Publication 2009/0075286, which are incorporated herein by reference in their entirety.

Another aspect of the invention is compositions for controlling harmful algae and HAB. The compositions of the invention comprise one or more PCD inducers, such as an oxidizing agent and/or a nitric oxide delivery agent, and another component selected from among: (a) another algaecidal agent, or (b) an activator of the PCD inducer, or (c) a dispersant, or (d) a combination of two or more of the foregoing.

PCD Inducers

The PCD inducer used in the methods, compositions, and kits of the invention can be any agent or treatment that induces PCD in the harmful algae of concern (e.g., *K. brevis*). The PCD inducer may be, for example, an organic molecule or inorganic molecule, a small molecule such as a small organic molecule, or a macromolecule, such as a protein or peptide, or nucleic acid molecule (DNA or RNA). Examples of PCD inducers include, but are not limited to, oxidizing agents (also known as oxidizers) and nitric oxide (NO) delivery agents.

The term "NO delivery agent" refers to any agents capable of delivering nitric oxide or a functional equivalent of NO, to the situs or algae of concern such that it is capable of inducing the PCD pathway. Such compounds can also be referred to as "NO donors" which is inclusive of a variety of NO donors including, but not limited to, organic NO donors, inorganic NO donors and prodrug forms of NO donors, "NO prodrugs", "NO producing agents", "NO delivering compounds", "NO generating agents", "NO providers", and NO mimetics. The term "NO delivery agent" is inclusive of NO (i.e., NO is itself an NO delivery agent).

NO delivery agents include those agents that generate or release NO or a functional equivalent through biotransformation by organisms at the intended site of action (biotransforming organisms, such as algae (the harmful algae of concern or another algae) and/or other organisms, which may be naturally present or applied). NO delivery agents include those that generate NO or a functional equivalent thereof spontaneously, or spontaneously release NO or a functional equivalent thereof. NO delivery agents include agents that in any other manner generate NO or a NO-like moiety or activates other stages of the NO pathway; or any agent which enables or facilitates NO utilization by the algae cell, when administered to the harmful algae of concern or to another organism. In some embodiments, the NO delivery agent is a type that spontaneously releases NO or a functional equivalent of NO. In some embodiments, the NO delivery agent is a type that releases NO or a functional equivalent of NO in an extended or sustained manner. In some embodiments, the NO delivery agent is one that releases NO or a functional equivalent of NO only in the presence of an activator.

Examples of NO delivery agents include, but are not limited to: organonitrates such as nitroglycerin (GTN), isosorbide mononitrates (ISMN) which include isosorbide 2-mononitrate (IS2N) and/or isosorbide 5-mononitrate (ISSN), isosorbide dinitrate (ISDN), pentaerythritol tetranitrate (PETN), erthrityl tetranitrate (ETN); ethylene glycol dinitrate, isopropyl nitrate, glyceryl-1-mononitrate, glyceryl-1,2-dinitrate, glyceryl-1,3-dinitrate, butane-1,2,4-triol trinitrate, amino acid derivatives such as N-hydroxyl-L-arginine (NOHA), $N^6$-(1-iminoethyl) lysine) (L-NIL), $L^5$-(1-iminoethyl) ornithine (LN-NIO), and S-nitrosoglutathione (SNOG); compounds that serve as physiological precursors of nitric oxide, such as L-arginine, L-citrulline and salts of L-arginine and L-citrulline; and other compounds which generate or release NO under physiologic conditions such as S,S-dinitrosodithiol (SSDD), [N-[2-(nitroxyethyl)]-3-pyridinecarboxamide (nicorandil), sodium nitroprusside (SNP), hydroxyguanidine sulfate, N,O-diacetyl-N-hydroxy-4-chlorobenzenesulfonamide, S-nitroso-N-acetylpenicilamine (SNAP), 3-morpholino-sydnonimine (SIN-1), molsidomine, Diethylamine (DEA)-NONOate (sodium N-(diethylamino)-N-oxidonitrous amide), (*)-(E)-ethyl-2-[(E)-hydroxyimino]-5-nitro-3-hexeneamide, (*)-N-[(E)-4-ethyl-3-[(Z)-hydroxyimino]-5-nitro-3-hexen-1-yl]-3-pyridinec-arboxamide, 4-hydroxymethyl-3-furoxancarboxamide and spermine NONOate (N-[4-[1-(3-aminopropyl)-2-hydroxy-2-nitrosohydrazino]butyl-1,3-propanedi-amine). PCD can also be induced by emitting NO directly to an aquatic medium, e.g., by bubbling NO gas through the medium.

For purposes of the present invention, by the term "NO mimetic" it is meant a functional equivalent of NO, any compound which mimics the effects of NO, compounds which act as a nitric oxide pathway mimetic, that has nitric oxide-like activity, or that mimics the effect of nitric oxide. Such compounds may not necessarily release, generate or provide nitric oxide, but they have a similar effect to nitric oxide on a pathway that is affected by nitric oxide. For example, nitric oxide has both cyclic GMP-dependent and cyclic GMP-independent effects. Nitric oxide is known to activate the soluble form of guanylyl cyclase thereby increasing intracellular levels of the second messenger cyclic GMP and other interactions with other intracellular second messengers such as cyclic AMP. As such, compounds which directly activate either particulate or soluble guanylyl cyclase such as natriuretic peptides (ANP, BNP, and CNP), 3-(5'-hydroxymethyl-2'furyl)-1-benzyl indazole (YC-cGMP or YC-1) and 8-(4-chlorophenylthio)guanosine 3',5'-cyclic monophosphate (8-PCPT-cGMP), are also examples of NO-mimetics. Nitric oxide mimetic activity encompasses those signal transduction processes or pathways which comprise at least one NO mimetic-binding effector molecule, such as for example, guanylyl cyclase and other heme containing proteins. Example of agents which function as NO mimetics by enabling or facilitating NO utilization by the cell are compounds which inhibit phosphodiesterase activity and/or expression, such as phosphodiesterase inhibitors.

In some embodiments, the NO delivery agent is an NO donor selected from among (±)-(E)-4-Ethyl-2-[(E)-hydroxyimino]-5-nitro-3-hexenamide; (±)-(E)-4-Ethyl-2-[(Z)-hydroxyimino]-nitro-3-hexen-1-yl-nicotinamide; 3,3-Bis(aminoethyl)-1-hydroxy-2-oxo-1-triazen e; 3-Ethyl-3-(ethylaminoethyl)-1-hydroxy-2-oxo-1-triazene; 3-Morpholinosydnonimine hydrochloride; 4-Phenyl-3-furoxancarbonitrile; Diethylamine NONOate sodium salt hydrate crystalline; Diethylenetriamine/nitric oxide adduct; Dipropylenetriamine NONOate; Isosorbide dinitrate; MAHMA NONOate; Molsidomine; S-Nitroso-N-acetyl-DL-penicillamine; S-Nitrosoglutathione'Sodium nitroferricyanide(III) dihydrate ACS reagent; Spermine-Nitric oxide complex hydrate; Streptozocin; Sulfo NONOate disodium salt; V-Pyrro/NO; AcOM-DEA/NO ($O^2$-(Acetoxymethyl) 1-(N,N-Diethylamino)diazen-1-ium-1,2-diolate); DEA/NO (Sodium (Z)-1-(N,N-Diethylamino)diazen-1-ium-1,2-diolate); Deta-NO (1-[N-(2-Amino ethyl)-N-(2-ammonioethyl) amino]diazen-1-ium-1,2-diolate); DPTA/NO (also NOC-19) (1-[N-(3-Aminopropyl)-N-(3-ammoniopropyl]diazen-1-ium-1,2-diolate; Hrabie-X-46-A (also NOC-5)(1-Hydroxy-2-oxo-3-(3-aminopropyl)-3-isopropyl-1-triazene); Hrabie-X-54-A (also NOC-7)(1-Hydroxy-2-oxo-3-(N-methyl-3-aminopropyl)-3-methyl-1-triazene; Hrabie-X-64-A (also NOC-12) (1-Hydroxy-2-oxo-3-(N-ethyl-2-aminoethyl)-3-ethyl-1-triazene); JS-K ($O^2$-(2,4-Dinitrophenyl) 1-[(4-Ethoxycarbonyl)piperazin-1-yl]diazen-1-ium-1,2-diolate); PAPA-NO (1-[N-(3-Ammoniopropyl)-N-(n-propyl)amino] diazen-1-ium-1,2-diolate); PROLI/NO (1-[(2-Carboxylato) pyrrolidin-1-yl]diazen-1-ium-1,2-diolate); SPER/NO (1-{N-[3-Aminopropyl]-N-[4-(3-aminopropylammoniobutyl)] }diazen-1-ium-1,2-diolate); and a mixture of sodium nitrite and ascorbic acid.

Other NO delivery agents that may be used include those NO donors described in Wang et al., 2002, Nitric Oxide Donors: Chemical Activities and Biological Applications, *Chemical Reviews*, 102:1091-1134; Nitric Oxide Donors: For Phainiaceutical and Biological Applications, edited by Peng G. Wang, Tingwei B. Cai, and Naoyuki Taniguchi, Wiley, John and Sons, Inc., April 2005; and Nitric Oxide Donors and Scavengers, CALBIOCHEM Technical Bulletin CB0562-0901 (which are each incorporated herein by reference in their entirety). In some embodiments, the applied NO delivery agent is one that augments the action of intracellularly (e.g., endogenously) released NO.

In some embodiments, the PCD inducer is not NO. In some embodiments, the PCD inducer is not an NO delivery agent.

Any agent that transfers oxygen atoms (an oxidizing agent) may be used as a PCD inducer in the methods, compositions, and kits of the invention. The oxidizing agent may generate active oxygen, hydroxyl radicals, ozone, chlorine dioxide, or free halogen (hypohalous acid), for example. Oxidizing agents include those agents that require in situ activation to act as oxidizers. Examples of oxidizing agent include, but are not limited to, sodium persulfate, potassium persulfate, ammonium persulfate, sodium percarbonate, sodium perborate, calcium hypochlorite, sodium dichloroisocyanuric acid, trichloroisocyanuric acid, ammonium monopersulfate, and hydrogen peroxide ($H_2O_2$) and other peroxide compounds.

Additional examples of oxidizing agents include potassium nitrate ($KNO_3$), hypochlorite and other hypohalite compounds such as bleach, iodine and other halogens (in oxidizing ability, the halogens follow the expected order: $F_2 > Cl_2 > Br_2 > I_2$) chlorite, chlorate, perchlorate and other analogous halogen compounds, permanganate salts, ammonium cerium(IV) nitrate and related cerium(IV) compounds, hexavalent chromium compounds such as chromium and dichromic acids and chromium trioxide, pyridinium chlorochromate (PCC), chromate/dichromate compounds, Tolien's reagent, sulfoxides, persulfuric acid, ozone, osmium tetroxide ($OsO_4$), nitric acid, nitric oxide, $Ag^+$, and $Cu^{++}$.

One or more PCD inducers may be used. PCD inducers may also function to induce PCD by more than one mechanism. Some agents may function as both a nitric oxide delivery agent and an oxidizing agent, for example.

The methods, compositions, and kits of the invention may optionally incorporate an agent capable of in situ activation to form an active PCD inducer (e.g., activation into an active oxidizing agent or activation into an active nitric oxide delivery agent). "In situ activation" is defined herein as activation of an agent (referred to interchangeably herein as a precursor, prodrug, or inactive PCD inducer) into an active PCD inducer (e.g., an active oxidizing agent or nitric oxide delivery agent) upon contact with, or exposure to, an activator (also referred to herein as an initiator) such as water (e.g., salt water) or light (e.g., sunlight or fluorescent light). Depending upon the PCD inducer selected, activation may occur intracellularly (e.g., within the harmful algal cell) or extracellularly within the aquatic medium. Examples of such compounds capable of in situ activation to form an oxidizing agent include sodium persulfates, potassium persulfates, and ammonium persulfates. Some PCD inducers may require metabolic biotransformation, in which case, the activator is an organism (or enzyme, catalyst, or other activating compound produced by an organism) that biotransforms the agent to activate the inactive PCD inducer into an active PCD inducer. The activating organism may be one that inhabits the situs of application or the activating organism may be one that is applied to the algae or situs before, during, or after application of the inactive PCD inducer. In cases in which one or more enzymes, catalysts, or other activating compound(s) are responsible for activation of the inactive PCD inducer, the isolated enzyme(s), catalyst(s), or other activating compound(s) may be applied to the algae or situs before, during, or after application of the inactive PCD inducer. The activating organism(s) or compound(s) may be applied separately or in the same composition as the inactive PCD inducer. Methods of activating the inactive PCD inducers include, without limitation, bringing the activator and inactive PCD inducer into contact with one another.

Depending upon the PCD inducer selected for use, use of an activator inside or outside the harmful algal cell may not be necessary. For example, an NO activator within the cell is not necessary when a compound is used that releases NO into the liquid media which then may diffuse into the algal cell. Intracellular NO production is not a necessary step or component of the process. However, that does not preclude the use of an NO activator that elicits NO production within the algal cell for HAB control. Without being limited by theory, it is possible that, in a natural cascade of events, intracellular NO production may occur as part of the PCD signaling pathway. In some embodiments, applying the PCD inducer comprises releasing nitric oxide (NO) directly into the situs (e.g., aquatic medium), or releasing the NO into the situs indirectly via an NO delivery agent.

Methods and Formulations for Control of Harmful Algae Blooms

Control of harmful algae and HAB using PCD inducers can be accomplished by a variety of methods known to those skilled in the art for applying algaecidal agents. These methods include, for example, the application of an algaecidally effective amount of PCD inducer(s) such as nitric oxide delivery agents and/or oxidizing agents, or compositions containing them, to the algae and/or situs. The PCD inducers and compositions containing them can be applied to an algae-contaminated situs or to a situs that is not currently contaminated.

The PCD inducers and compositions containing them can be applied to the algae and/or aquatic environment by any of a variety of methods, such as spraying, dusting, sprinkling, mixing, mechanically or manually broadcasting over the surface of the water, adding the PCD inducer to the filter media, filtration system, or skimmer with the circulation system running, pre-diluting in water, placing in a chemical feeding device through which the water is pumped and, if necessary, dissolving the PCD inducer and PCD inducer-containing composition, and adding to the aquatic environment or adding by means of an automated dosing system.

Manual broadcasting is particularly advantageous because no special electrical equipment is needed. A further advantage of manual feeding is that the PCD inducers or inducer-containing compositions can be applied directly in contact with algal masses that are floating on the surface of the water or just under the surface of the water. Typically, during manual broadcasting, a scoop is used to sprinkle the product to the areas where it is needed. Since floating algae tends to accumulate at the edges of water bodies, the PCD inducers may be applied by manually broadcasting from the water's edge. For larger bodies of water, depending upon the depth, waders or a boat may be used to assist in delivering the compositions to the areas needed.

The controlled addition of a PCD inducer, such as NO, to an aquatic environment may treat or protect the environment from harmful algae, leading to increased survivability of susceptible organisms within the area of effect, such as fish and shellfish. In cases in which the PCD inducer utilized is NO, the NO can be introduced to the aquatic environment alone or with another gas, such as oxygen.

In some embodiments of the method of the invention, an apparatus is used to apply a PCD inducer to the harmful algae, the situs which the harmful algae inhabits or potentially inhabits, or to both the harmful algae and the situs, wherein the apparatus includes an injector for release of a PCD inducer (such as NO), and a source of the PCD inducer (such as an NO source), wherein the injector is in flow communication with the PCD inducer source. Preferably, the injector is adapted to occupy the situs or potential situs of the harmful algae.

U.S. Pat. No. 6,918,354 (Perriello), which is incorporated herein by reference in its entirety, discloses a method and apparatus for butane-enhanced aquatic plant and animal growth. The method and apparatus in U.S. Pat. No. 6,918,354 can be modified for control of harmful algae and HAB by substituting the alkane source with a source of PCD inducer, such as a source of NO.

The dosage of PCD inducer will depend on the amount of aquatic medium to be treated and the amount of algal growth in the aquatic medium to be treated. The frequency of treatment will also depend on the amount of algal growth in the aquatic medium to be treated. Depending on conditions such as temperature and exposure to sunlight, certain bodies of water may require more frequent treatment to control the algae. The aquatic medium can be re-treated whenever the algae start to re-infest the medium, or before.

The PCD inducers and compositions containing them can be applied in any physical state (e.g., solid, liquid, semi-solid) that will permit their function in inducing apoptosis in target algae, at the situs (e.g., within the aquatic medium). For example, PCD inducers and compositions can be applied in powder form, or stored in powder form and mixed with water or another carrier and/or agent for application to the algae or situs. PCD inducers and compositions in granular or tablet form offer the advantage of slow and controlled release, more effectively delivering a continuous level of PCD inducer. Delivery (application) can be carried out by skimmer, floater or erosion-type or automated feeders, for example. Granular and tablet forms also offer lower shipping weight, less storage space, minimal spill hazards, and generally safer handling.

The use of the nitric oxide delivery compounds and/or oxidizing agents to induce PCD and thereby control HAB can be accomplished readily by those skilled in the art having the benefit of the instant disclosure. For example, the compounds may be encapsulated, incorporated in a granular form, solubilized in water or other appropriate solvent, powdered, and included into any appropriate formulation for direct application to the algae or to an algae-inhabited locus.

The compositions of the present invention may also contain other additives, such as those known in the water treatment art. These additives include but are not limited to pigments, dissolution rate modifiers, binders, lubricants, color-containing salts, biocides, buffers, chelating agents, other algaecides (PCD-inducing or non-PCD inducing), fungicides, sequestering agents, clarifiers, enzymes, dyes, fragrances, surfactants, dispersants (e.g., biodispersants), biopenetrants, sorbitan monostearate, sulfamic acid, tallowpropylamine diamine, cocopropylamine diamine, oleylpropylamine diamine, stearyldimethylbenzylammonium chloride, and combinations thereof. These additives may be pre-blended with any of the components of the composition, and are generally present in the composition of the invention in amounts ranging from 0.2 to 10 weight percent.

The additional algaecidal agent may be, for example, a flocculant (such as clay or polyaluminum chloride (PAC)), which causes formation of larger algal aggregates, which settle and further entrain cells during their descent.

The additive may be a deflocculant. The term "defloccu-lant" refers to a substance that, when added to scattered particles in suspension, causes a reduction in apparent viscosity. Deflocculants are substances that prevent flocculation by increasing zeta potential and therefore the repulsive forces between particles. Deflocculants can act via a combination of mechanisms and can be organic or inorganic in nature. Table 1 lists examples of deflocculants.

TABLE 1

| Deflocculants | |
| --- | --- |
| Organic | Inorganic |
| Humic acids and derivatives | Sodium and potassium carbonates |
| Alkaline lignosulfonates | Sodium and potassium hydroxides |
| Tannin compounds | Sodium silicates |
| Polyacrylates and acrylic derivatives | Phosphates and polyphosphates |
| Polycarbonates | Sodium and ammonium oxalates |
| Sodium citrate | |
| Gum Arabic | |
| Low viscosity Na-CMC | |

The dispersant may be a biodispersant. Biodispersants are typically non-ionic or anionic surfactants (e.g., ethylene oxide/propylene oxide copolymers) that stabilize or disperse particles.

As used herein, the term "algaecidally effective" is used to indicate an amount or concentration of an algaecidal compound, such as an inducer of programmed cell death, which is sufficient to reduce the algae population in a geographical locus as compared to a corresponding geographical locus in the absence of the amount or concentration of the algicidal compound. To be algaecidally effective, complete killing of target algae populations may not be required. For example, compromising the algae's ability to compete for nutrients may be sufficient.

The term "algaecidal" is not intended to refer only to the ability to kill algae, but also includes the ability to interfere with the algal life cycle and/or life cycle of the HAB in any way that results in an overall reduction in the algae population. For example, the term "algaecidal" includes inhibition of a dinoflagellate from progressing from one form to a more mature form. Further, the term "algaecidal" is intended to encompass anti-algae activity during all phases of an algae's or HAB's life cycle.

The methods, compositions, apparatus, and kits of the invention can also incorporate other methods and/or agents for controlling HAB before, during, or after application of the PCD inducer(s). For example, it is known that the addition of barley straw to water environments will decrease the algae bloom through the natural decomposition of the straw into humeric compounds. It is also known to use a process for the aqueous extract of barley straw, and a process of partially decomposed barley straw inoculated with bacteria. Coloring agents or water soluble dyes may be used in an attempt to absorb the wavelengths of light that are preferred by planktonic algae. Various chemical herbicides and/or algaecides may be used. Such agents can be applied in the same composition as the PCD inducer or in a separate composition(s).

The PCD inducer(s) used in the methods, compositions, apparatus, and kits of the invention can be applied in various forms, including those which allow for extended or sustained release of the PCD inducer(s). For example, nitric oxide-releasing films and nanoparticles may be utilized. PCD inducers can be applied to various substrates, including solid or semi-solid substrates, such as filters or filtration systems, and placed in contact with the aquatic medium.

It should be understood that the term "red tide" is a colloquial term used to refer to a harmful algal bloom or HAB. The term "red tide" is being phased out in favor of the more accurate term, HAB, because red tides are not necessarily red and may have no discoloration at all, they are unrelated to movements of the tides, and a wide variety of algal species are known bloom-formers. In some embodiments, the HAB species is the dinoflagellate *Karenia brevis*, which is common to the eastern Gulf of Mexico. In some embodiments, the HAB species is *Alexandrium fundyense*, which is common to the northern east coast of the United States, particularly the Gulf of Maine. In some embodiments, the HAB species is *Skeletonema costatum*. In some embodiments, the HAB species is one other than *Skeletonema costatum*. In some embodiments, the harmful algae is not one or more algae selected from the group consisting of *Skletonema costatum, Dicrateria zhanjiangensis nov.* sp., *Platymonas subcordiformis*, and *Emiliania huxleyi*.

Another aspect of the invention includes kits for detecting harmful algae and/or for determining algal susceptibility to PCD induction. The kits of the invention comprise one or more PCD inducers and one or more reagents useful for determining the presence of a harmful algae. Preferably, the one or more PCD inducers and reagents are packaged together. The packaging may include receptacles (e.g., plastic bottles, wells, or other containers) for the PCD inducers, reagents, and/or other components.

In some embodiments, the one or more reagents include antibodies (e.g., immobilized antibodies or an ELISA plate), and/or PCR primers, and/or a molecular beacon, for determining the presence of a harmful algae. For example, the one or more reagents can include one or more reagents necessary for determining the presence of *K. brevis* as described in U.S. Pat. No. 7,422,857, Paul, J., issued to the University of South Florida).

Optionally, the kit includes a sample collection device, which may be used to collect a sample of algae and/or aquatic medium to be tested (e.g., ocean water). The collected sample can be tested for the presence of one or more harmful algae. Likewise, harmful algae present in the sample can be tested for susceptibility to control (e.g., mitigation or termination) by one or more PCD inducers.

Optionally, the kit includes instructions pertaining to the use of one or more of the packaged components, e.g., for applying the PCD inducer, or determining the presence of a harmful algae, or both.

Another aspect of the invention includes an apparatus for control of harmful algae and harmful algal bloom (HAB), comprising an injector for release of an inducer of programmed cell death (PCD inducer) and a source of the PCD inducer, such as an NO source, wherein the injector is in flow communication with said PCD inducer source. Flow communication between the PCD inducer source and the injector can be via one or more pipes, tubes, or other conduit. A valve can be included to control the flow of the PCD inducer. A gas source, such as an air pump, can also be connected to the tube through a valve. A controller can be used to control operation of valves of the apparatus. The controller can include a timer that controls the timing of the operation of one or more of the valves. The PCD inducer source can be a tank containing the PCD inducer. The PCD inducer can be stored and applied to the situs through the injector in solid, liquid, or gas form, as appropriate to the PCD inducer and the conditions in the situs. The PCD inducer can be applied alone or in a vehicle, such as a carrier fluid.

As indicated above, U.S. Pat. No. 6,918,354 (Perriello) discloses a method and apparatus for enhancing aquatic plant and animal growth using an alkane such as butane. The method and apparatus in U.S. Pat. No. 6,918,354 can be modified for control of harmful algae and HAB by substituting the alkane source with a source of PCD inducer, such as a source of NO, as described herein. FIG. 6 of U.S. Pat. No. 6,918,354 is a schematic representation of that apparatus.

Preferably, the injector is adapted to occupy the situs or potential situs of the harmful algae. The injector may be stationary, or part of a mobile device (e.g., submersible vehicles such as remotely operated vehicles, automated underwater vehicles, and manned submersibles) that moves through the situs (e.g., at various zones and/or depths within a water column). For example, one or more injectors can be strategically placed around and/or within a desired area. Injector placement can be optimized based upon a variety of factors, such as the particular environment and the behavior of the PCD inducer within the environment (e.g., buoyancy characteristics). In embodiments in which the PCD inducer is a gas, such as NO, it may be desirable to place one or more injectors at the bottom of a water column so that the gas bubbles rise upward through the desired area. Various forms of injectors can be used, including injectors having a proximal end for receiving the PCD inducer from the PCD inducer source, and a distal end for dispersing the PCD inducer. The distal end can include a plurality of openings. In embodiments in which the PCD inducer is a gas (e.g., NO gas), the injector preferably includes a gas diffuser to produce a large surface area (large gas-liquid interface area), facilitating rapid mass transport of gas into the situs, and creating numerous gas bubbles. The PCD inducer may be injected into the situs alone, simultaneously, or intermittently with other agents such as dispersants, algaecides, activators of the PCD inducer, etc.

In some embodiments, the apparatus further comprises a sensor for detecting the presence of harmful algae within the situs. Optionally, the sensor is in operable communication with the injector such that a PCD inducer is released from the injector into the situs upon detection of harmful algae by the sensor. In some embodiments, the sensor detects the presence of at least one toxin or other biomarker produced by the harmful algae at the situs. In some embodiments, the toxin comprises a brevetoxin.

In some embodiments, the apparatus further comprises a sensor for measuring the amount or concentration of PCD inducer (e.g., NO) at the situs.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1

Induction of Programmed Cell Death in *Karenia Brevis* (Piney Island A2 Strain)

Nitric oxide (NO) has been shown to promote or inhibit the growth of some microalgae (*Skeletonema costatum, Dicrateria zhanjiangensis nov*. sp., *Platymonas subcordiformis*, and *Emiliani huxleyi*) when NO of different concentrations was added one or two times each day during the cultivation process (Zhang Z. et al., 2003, *Oceanic and Coastal Sea Research,* 2(2):185-188). More recently, NO was shown to induce expression of a death specific protein in *Skeletonema costatum* (Chung, C. C. et al., 2008, *Applied and Environmental Microbiology,* 74(20:6521-6527). It appears that nitric oxide (NO) is a crucial secondary messenger that signals expression of the protein ScDSP-1 in this diatom.

The present inventors have determined that NO may be used to trigger cell death in *Karenia brevis* and potentially other harmful algae. The response to low concentrations occurs within 24 hours and varies with concentration. To describe the dose response, cultures of *K. brevis* (Piney Island A2) were exposed to varied concentrations of the nitric oxide donor diethylamine NONOate sodium salt hydrate or DEA NONOate (IUPAC name: sodium N-(diethylamino)-N-oxidonitrous amide).

Work described by Chung et al. (2008) employed 500 μM DEA NO to elicit ScDSP-1 expression in *Skeletonema costatum*. The present inventors sought to determine the low end of the dose response, if any effect, in *K. brevis*. Trials therefore tested the effect of DEA NONOate concentrations ranging from 100 μM to 0.1 μM. For each trial, *K. brevis* cultures were grown in L1 media. Cultures were diluted 1:1 from a stock flask into a total volume of 125 mL in 250-mL acid washed and autoclaved flasks. Cultures were allowed to recover for 2-4 days prior to treatment. Immediately prior to treatment, DEA NONOate (Sigma-Aldrich, St. Louis, Mo.) was dissolved from its powdered form in sterile nuclease-free water. The solution was made to a concentration of 1 mg $mL^{-1}$. Two trials were performed to delineate responses to different concentrations of NO. In each case, the appropriate volume of DEA NONO solution was added and the cultured swirled by hand gently to mix the solution. Control flasks were also used for each trial; these received only an aliquot of the water used for dissolving DEA NONOate, equal to the largest volume administered to treatment flasks for that trial. At the concentration of 1 mg $mL^{-1}$, volumes of DEA NONO solution added ranged from 1.9 mL to 1.9 μL for 100 μM to 0.1 μM final concentrations in culture flasks. Three replicate flasks were used for each concentration and negative controls. Prior to treatment and at each sampling point after treatment, 5 mL of culture were removed for counting. A 1 mL aliquot was imaged/counted on the FlowCam flow-through microscope and the remainder was stained with Lugol's iodine solution and counted by light microscope on a gridded Sedgewick counting slide (1 mm$^2$ grid size). For slide counting, 50-70 grid squares were counted for each sample. Although counts were obtained for most samples by FlowCam and light microscopy, the light microscope counts were used for recording quantitative data while FlowCam images were used as a record of cell appearances.

Figure 2A:
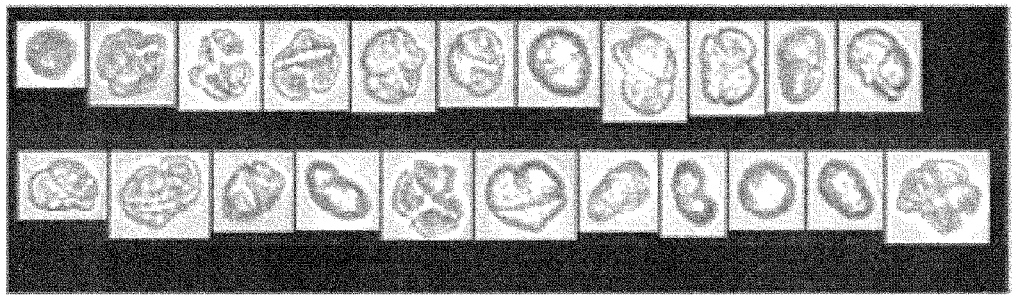
FIGS. 2A-2B show images of treated and untreated *K. brevis* cells.
Figure 2B:
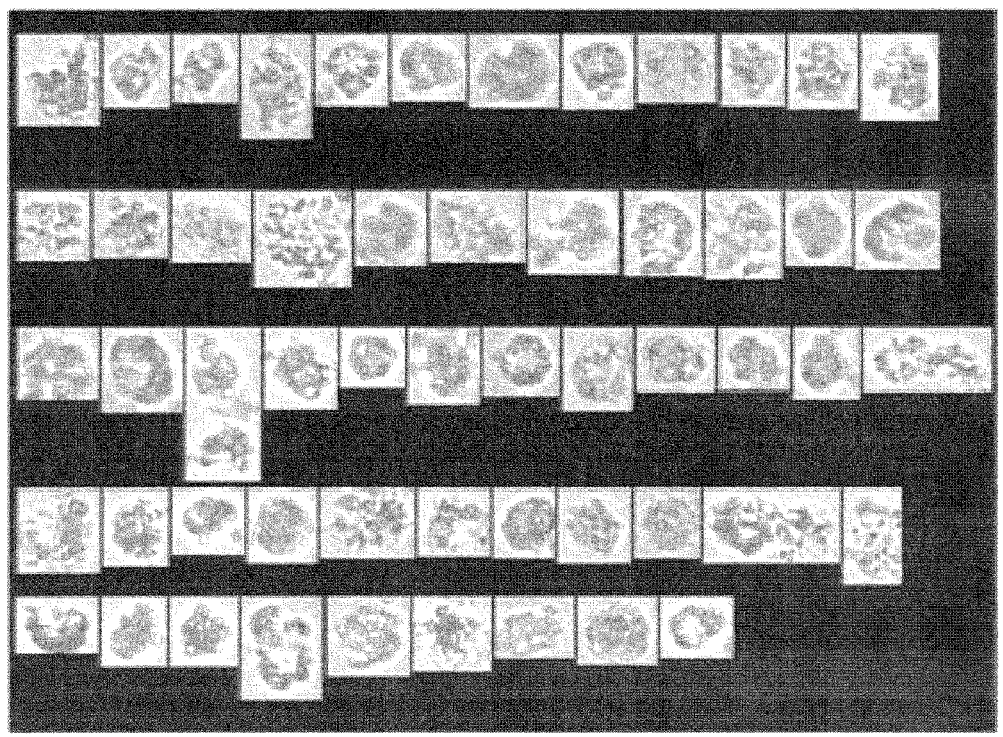

An initial trial tested only the highest concentration of 100 μM (results shown in FIG. 1). By 1 day post-treatment, no intact cells were observed. Samples were also taken at 2 days post-treatment, and no intact cells were observed. Cell remnants were present but easily differentiated from intact cells by appearance. FIGS. 2A-2B show images taken from the FlowCam, indicating the difference between intact cells in the control flask (FIG. 2A) vs. disrupted cells in the treated flasks (FIG. 2B). The images are a sub-sampling, but in treated flasks all particles imaged by the FlowCam resembled the disrupted cells.

Figure 3:
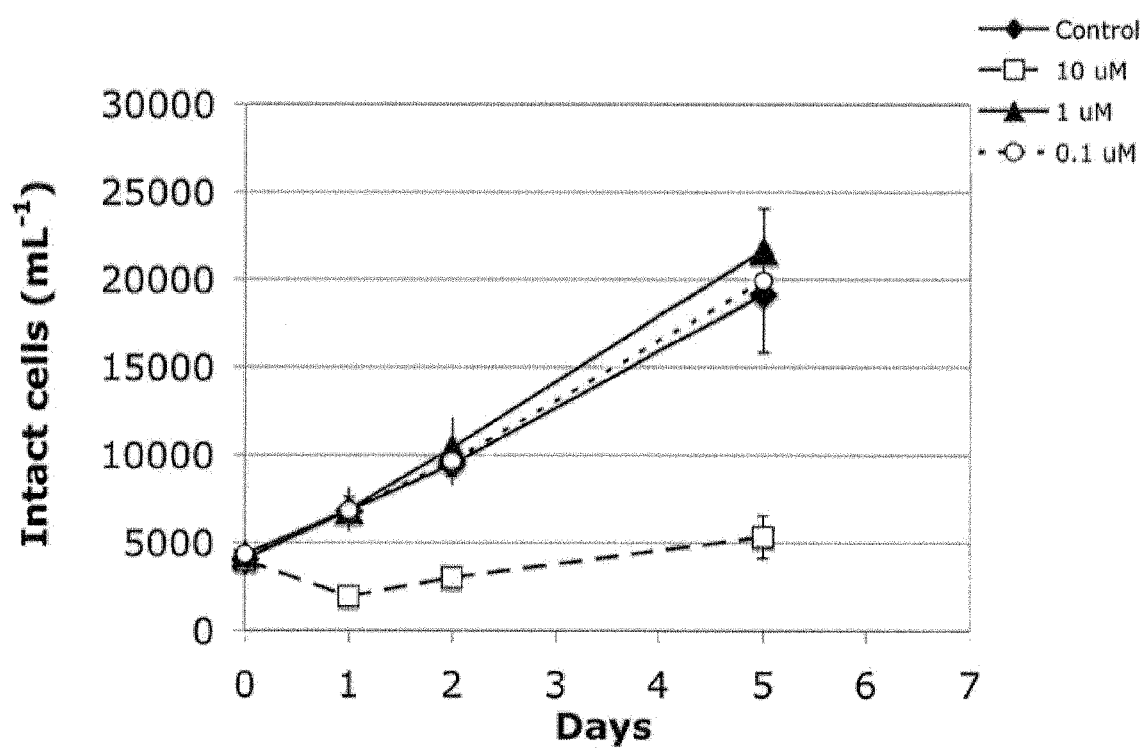
FIG. 3 shows results from treatment of *K. brevis* cultures with 0.1 µM, 1 µM, and 10 µM NO, along with untreated control (0 µM). Intact cell counts on days 1, 2, and 5 post-treatment are shown. Error bars are 1 standard deviation about the average of three replicates for each treatment concentration. 10 µM NO resulted in approximately 50% mortality. Lower concentrations had no effect.
Figure 4:
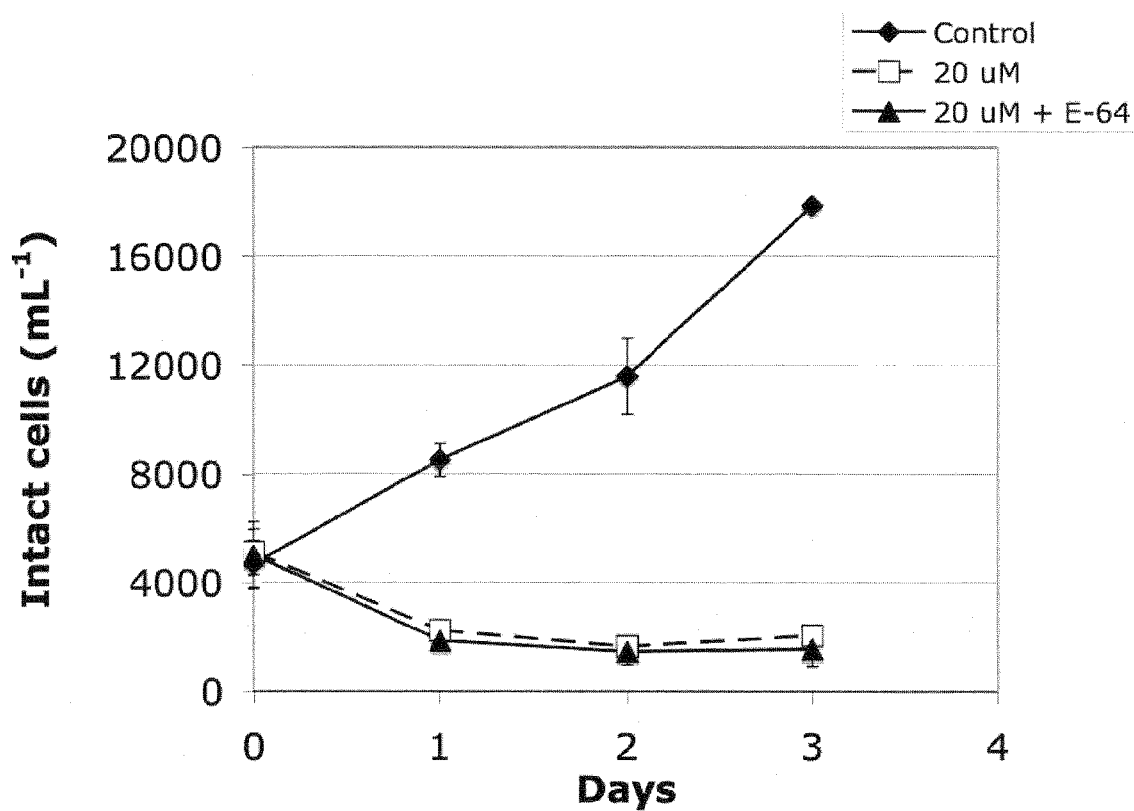
FIG. 4 shows results of treatment of *K. brevis* with the protease inhibitor E-64. 20 µM NO produced about 50% mortality. The addition of the cystein-protease inhibitor E-64 at a concentration of 10 µM provided no protection.

A second trial tested the effects of lower NO concentrations on *K. brevis* cells (results shown in FIG. 3). Among those concentrations tested, only 10 μM NO produced an observable effect on viable/intact cell counts. Intact cells were reduced by approximately 50% from pre-treatment numbers. The surviving cells appeared to recover as by T=5 days, cell counts had increased to greater than pre-treatment numbers. Lower concentrations of 1 μM NO or less appear to have no effect on *K. brevis* in culture; changes in intact cell numbers in these flasks were not significantly different from untreated cultures.

To test an additional intermediate concentration of NO, a flask was treated with 20 μM DEA NONO final concentration. In this trial, higher-density cultures (controls from the previous trial) were treated. The average intact cell count from two treated replicates at T=2 days was a decrease of 98.6% from pre-treatment counts (+/−0.18%) whereas a single untreated control reflected a decrease of 6.3% over the same time. Thus, the effective minimum concentration was between 10 uM and 20 uM.

To test whether the cystein-protease inhibition has any effect on NO-induced mortality in *K. brevis*, the cystein-protein inhibitor E-64 (L-transepoxysuccinyl-leucylamido-[4-guanidino]butane) was added at a concentration of 10 μM. FIG. 4 shows 20 μM NO produced about 50% mortality in *K. brevis*. The addition of E-64 provided no protection against mortality.

Example 2

Caspase-Like Enzyme Activity in *Karenia brevis* (Piney Island A2 Strain)

Caspase-like activity has been found to be strongly correlated with the production of NO in thermally challenged *Symbiodinium microadriaticum* (not an HAB former), and pretreatment of the microalgae with the caspase 3-specific inhibitor, Ac-DEVD-CHO, before supplementation of NO donors prevented increase in caspase-like activity (Bouchard J. N. et al., 2009, *Mar. Biol.,* 156:2220). Since caspase activity is a hallmark of PCD, experiments were conducted to examine caspase-like enzyme activity in *K. brevis*. The activity of enzymes that are similar to caspase-3 and caspase-8 were examined. The assays use a commercially available kit (MBL International, Woburn, Mass.) to measure the protease activity specific to certain amino acid sequence motifs. A short time series was performed to measure upregulation of caspase-like activity due to exposure to NO. NO was produced from the compound DEA-NONOate (use of this is previously described herein). Table 2 shows the effects of nitric oxide on caspase-like enzyme activity. Based on these findings, there is at least a 2-3 fold up-regulation of caspase-like activity due to NO exposure at 50-100 micromolar. This provides evidence that *K. brevis* death due to NO exposure is mediated by PCD pathways in the cells. This activity appears rapidly (within 20 minutes), and can decline rapidly (by 120 minutes). The decline is presumably due to actual death of the cells, since at the 120 minute mark, many cells were already in the process of lysis when viewed microscopically.

TABLE 2

| | Absorbance of colorimetric caspase cleavage product | | Upregulation vs. control (fold) | |
|---|---|---|---|---|
| | caspase 3 | caspase 8 | caspase 3 | caspase 8 |
| Experiment 1: 100 uM NO | | | | |
| control (no NO) | 0.001 | 0.007 | 1 | 1 |
| 60 min | 0.014 | 0.017 | 14 | 2.4 |
| 120 min | 0.001 | 0.006 | 1 | 0.9 |
| Experiment 2: 50 uM NO | | | | |
| control | 0.006 | 0.01 | 1 | 1 |
| 20 min | 0.016 | 0.021 | 2.7 | 2.1 |
| 40 min | 0.016 | 0.019 | 2.7 | 1.9 |
| 60 min | 0.013 | 0.018 | 2.2 | 1.8 |

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

We claim:

1. A method for controlling harmful algae and harmful algal bloom (HAB), comprising applying an inducer of programmed cell death (PCD inducer) to the harmful algae, to the situs which the harmful algae inhabits or potentially inhabits, or to both the harmful algae and the situs, wherein the PCD inducer comprises: an NO delivery agent comprising sodium N-(diethylamino)-N-oxidonitrous amide, or a mixture of sodium nitrite and ascorbic acid, or both.

2. The method of claim 1, wherein the PCD inducer further comprises an oxidizing agent, and the oxidizing agent comprises peroxide, or hypochlorite, or both.

3. The method of claim 1, wherein said applying comprises applying the PCD inducer to the situs which the harmful algae inhabits or potentially inhabits.

4. The method of claim 1, wherein said applying comprises applying the PCD inducer to the situs which the harmful algae inhabits or potentially inhabits, and wherein the situs is an aquatic medium comprising marine water, fresh water, or brackish water.

5. The method of claim 1, wherein said applying comprises applying the PCD inducer to the situs which the harmful algae inhabits or potentially inhabits, and wherein the situs is a culture, field sample, aquarium, aquaculture system, waste water, cooling tower, water holding or conveying system, water filter medium, pool, spa, or fountain.

6. The method of claim 1, wherein said applying comprises applying the PCD inducer to the situs which the harmful algae inhabits or potentially inhabits, and wherein the situs is a body of water selected from the group consisting of ocean, bay, estuary, pond, lagoon, lake, river, stream, and canal.

7. The method of claim 1, wherein the harmful algae is one or more algae selected from among *Alexandrium* sp., *Gymnodinium* sp, *Karenia mikimotoi*, *Pseudo-nitzschia* species, *Karenia seleniformes*, *Karenia bidigigata*, *Pyrodininum* sp., *Gonyaulax* sp., *Ceratium* species, *Lingulodinium*, *Chattonella* sp., *Akashiwo* sp., *Gyrodinium* sp., *Pfisteria* sp., *Prorocentrum* sp., *Dinophysis*, *Heterocapsa*, *Scripssiella*, and *Protoperidinium* sp.

8. The method of claim 1, wherein the harmful algae comprises *Karenia brevis*.

9. The method of claim 1, wherein the PCD inducer is applied to an HAB, and the HAB is mitigated or terminated.

10. The method of claim 1, wherein the PCD inducer is applied to the situs which the harmful algae inhabits before or after HAB formation.

11. The method of claim 1, wherein two or more PCD inducers are applied.

12. The method of claim 1, wherein an additional non-PCD inducing algaecide is applied before, during, or after application of the PCD inducer.

13. The method of claim 1, further comprising determining whether the harmful algae is present at the situs or in the vicinity of the situs.

14. The method of claim 13, wherein said determining comprises determining the presence of at least one toxin or other biomarker produced by the harmful algae at the situs or in a sample obtained from the situs.

15. The method of claim 13, wherein the at least one toxin comprises a brevetoxin.

16. The method of claim 13, wherein said determining comprises determining the presence of *Karenia brevis* polyketide synthetase RNA.

* * * * *

UNITED STATES PATENT AND TRADEMARK OFFICE
CERTIFICATE OF CORRECTION

PATENT NO. : 8,476,196 B2  
APPLICATION NO. : 12/831065  
DATED : July 2, 2013  
INVENTOR(S) : John H. Paul and David John Page 1 of 1

It is certified that error appears in the above-identified patent and that said Letters Patent is hereby corrected as shown below:

In the Specification

Column 7,  
Line 6, "isosorbide 5-mononitrate (ISSN)" should read --isosorbide 5-mononitrate (IS5N)--

Column 8,  
Line 30, "Phainiaceutical" should read --Pharmaceutical--  
Lines 61-62, "Tolien's reagent" should read --Tollen's reagent--

Signed and Sealed this  
Nineteenth Day of November, 2013

Teresa Stanek Rea  
*Deputy Director of the United States Patent and Trademark Office*